(12) United States Patent
Kamimura et al.

(10) Patent No.: US 6,562,803 B2
(45) Date of Patent: May 13, 2003

(54) HAIR-GROWING AGENT

(75) Inventors: Ayako Kamimura, Tsukuba (JP);
Tomoya Takahashi, Tsuchiura (JP);
Takashi Mimura, Shinagawa-ku (JP);
Shinkichi Honda, Nagareyama (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/073,107

(22) Filed: Feb. 12, 2002

(65) Prior Publication Data

US 2002/0155085 A1 Oct. 24, 2002

(30) Foreign Application Priority Data

Feb. 16, 2001 (JP) ......................... 2001-040350

(51) Int. Cl.$^7$ .............................................. A61K 31/66
(52) U.S. Cl. ...................... 514/119; 514/120; 514/121; 514/134
(58) Field of Search ................. 514/120, 134, 514/119, 121

(56) References Cited

U.S. PATENT DOCUMENTS

| | | | |
|---|---|---|---|
| 4,874,791 A | 10/1989 | Adachi et al. | 514/558 |
| 4,978,681 A | 12/1990 | Adachi et al. | 514/557 |
| 5,030,442 A | 7/1991 | Uster et al. | 424/45 |

FOREIGN PATENT DOCUMENTS

| | | | | |
|---|---|---|---|---|
| DE | 32 22 016 | 6/1982 | | |
| DE | 41 13 346 | 4/1991 | | |
| EP | 0 768 079 | 4/1997 | | |
| JP | 61-7205 | 1/1986 | | |
| JP | 61-15809 | 1/1986 | | |
| JP | 63-41363 | 8/1988 | | |
| WO | 96/00561 | 1/1996 | | |
| WO | 97/09989 | 3/1997 | | |
| WO | 01/12141 | * 2/2002 | ............ | A61K/7/06 |

OTHER PUBLICATIONS

Nishizawa et al, Chem. Abstr., No. 134:256599, 2001.*
Ke no lgaku, Medical Science of Hair, p. 283, Bunkodo (1987).
Hair Science, p. 80, Japan Hair Science Association (1986).
Fragrance Journal, p. 95–103 (1989).
Takashi, et al., Skin Pharmacology and Applied Skin Physiology, vol. 13, (2000), pp. 133–142.

* cited by examiner

*Primary Examiner*—James H Reamer
(74) *Attorney, Agent, or Firm*—Fitzpatrick, Cella, Harper & Scinto

(57) ABSTRACT

The present invention provides a hair-growing agent comprising, as an active ingredient, a phosphatidic acid represented by formula (I):

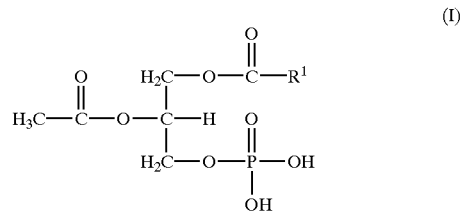

(wherein $R^1$ represents straight-chain alkyl having an odd number of carbon atoms, straight-chain alkenyl having an odd number of carbon atoms, or straight-chain alkynyl having an odd number of carbon atoms).

15 Claims, No Drawings

HAIR-GROWING AGENT

BACKGROUND OF THE INVENTION

The present invention relates to a hair-growing agent comprising a phosphatidic acid as an active ingredient.

A known example of a cosmetic or drug relating to hair which comprises a phosphatidic acid is a hair-nourishing agent comprising a phosphatidic acid having straight-chain fatty acid residues having an odd number of carbon atoms, that is, a phosphatidic acid represented by formula (II):

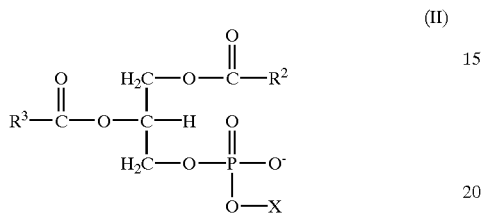

(wherein $R^2$ and $R^3$ each represents an aliphatic hydrocarbon group; and at least one of $R^2$ and $R^3$ is a straight-chain aliphatic hydrocarbon group having an even number of carbon atoms) (Japanese Published Examined Patent Application No. 41363/88). Japanese Published Unexamined Patent Application No. 7205/86 describes a cell activator comprising a phosphatidic acid having two branched-chain fatty acid residues as an active ingredient. However, there has not been known a hair-growing agent comprising a phosphatidic acid wherein all fatty acid residues are straight-chain fatty acid residues having an even number of carbon atoms and which has an acetyl group at the 2-position of the glycerin residue. Japanese Published Unexamined Patent Application No. 15809/86 describes a cell activator comprising a fatty acid having an odd number of carbon atoms, and biotin or vitamin B12 as active ingredients.

It is known that a phosphatidic acid is used as a vehicle for liposome preparation added to minoxidil which is a hair growth-activating component (U.S. Pat. No. 5,030,442), though not as an active ingredient of a hair-growing agent.

A mixture of some phospholipids including a phosphatidic acid is known to have hair loss-inhibiting activity (WO 97/09989). Also known is a hair-growing agent comprising a phospholipid mixture (DE 3222016, DE 4113346).

WO 96/00561 describes a hair-growing agent comprising proanthocyanidin. It is known that tocopherol ["Ke no Igaku" (Medical Science of Hair), p. 283, Bunkodo (1987); Hair Science, p. 80, Japan Hair Science Association (1986)], pantothenic acid and biotin [Fragrance Journal, p. 95–103, Fragrance Journal (1989)], and a protein kinase C-specific inhibitor [Skin Pharmacology and Applied Skin Physiology, 13, 133–142 (2000)] each have hair-growing activity. However, there is no report on a hair-growing agent comprising, as active ingredients, a phosphatidic acid, and one or more members selected from the group consisting of proanthocyanidin, tocopherol, derivatives of tocopherol, pantothenic acid, derivatives of pantothenic acid, protein kinase C-specific inhibitors or pharmaceutically acceptable salts thereof and biotin.

SUMMARY OF THE INVENTION

The present invention provides a hair-growing agent comprising a phosphatidic acid as an active ingredient, which has an excellent hair-growing effect, and a hair-growing agent comprising, as active ingredients, a phosphatidic acid, and one or more members selected from the group consisting of proanthocyanidin, tocopherol, derivatives of tocopherol, pantothenic acid, derivatives of pantothenic acid, protein kinase C-specific inhibitors or pharmaceutically acceptable salts thereof and biotin.

The present invention relates to the following subject matters.

(1) A hair-growing agent comprising, as an active ingredient, a phosphatidic acid represented by formula (I):

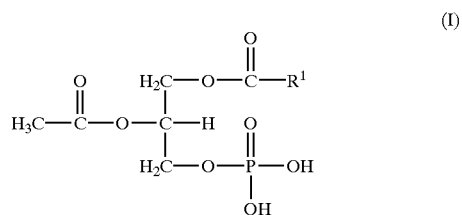

(wherein $R^1$ represents straight-chain alkyl having an odd number of carbon atoms, straight-chain alkenyl having an odd number of carbon atoms, or straight-chain alkynyl having an odd number of carbon atoms).

(2) The hair-growing agent according to the above (1), wherein the straight-chain alkyl having an odd number of carbon atoms is undecyl, tridecyl, pentadecyl or heptadecyl, and the straight-chain alkenyl having an odd number of carbon atoms is pentadecenyl or heptadecenyl.

(3) A hair-growing agent comprising, as active ingredients, the phosphatidic acid according to the above (1) or (2), and one or more members selected from the group consisting of proanthocyanidin, tocopherol, derivatives of tocopherol, pantothenic acid, derivatives of pantothenic acid, protein kinase C-specific inhibitors or pharmaceutically acceptable salts thereof and biotin.

(4) The hair-growing agent according to the above (1) or (2), further comprising proanthocyanidin.

(5) The hair-growing agent according to the above (4), wherein the proanthocyanidin is one or more members selected from the group consisting of procyanidin B-1, procyanidin B-2, procyanidin B-3, procyanidin C-1 and procyanidin C-2.

(6) The hair-growing agent according to any of the above (1), (2), (4) and (5), further comprising tocopherol or a derivative of tocopherol.

(7) The hair-growing agent according to the above (6), wherein the tocopherol or the derivative of tocopherol is one or more members selected from the group consisting of dl-α-tocopherol, d-α-tocopherol, dl-α-tocopherol acetate, d-α-tocopherol acetate and dl-α-tocopherol nicotinate.

(8) The hair-growing agent according to any of the above (1), (2) and (4) to (7), further comprising pantothenic acid or a derivative of pantothenic acid.

(9) The hair-growing agent according to the above (8), wherein the pantothenic acid or the derivative of pantothenic acid is one or more members selected from the group consisting of calcium pantothenate, sodium pantothenate, D-pantothenyl alcohol, DL-pantothenyl alcohol and pantothenyl ethyl ether.

(10) The hair-growing agent according to any of the above (1), (2) and (4) to (9), further comprising a protein kinase C-specific inhibitor or a pharmaceutically acceptable salt thereof.

(11) The hair-growing agent according to the above (10), wherein the protein kinase C-specific inhibitor is one or more members selected from the group consisting of calphostin C, hexadecylphosphocholine, palmitoyl-DL-carnitine and polymyxin B.

(12) The hair-growing agent according to any of the above (1), (2) and (4) to (11), further comprising biotin.

(13) The hair-growing agent according to any of the above (1) to (12), which does not substantially comprise minoxidil.

(14) A method for stimulating hair growth in a mammal, which comprises applying to the skin of said mammal a phosphatidic acid represented by formula (I):

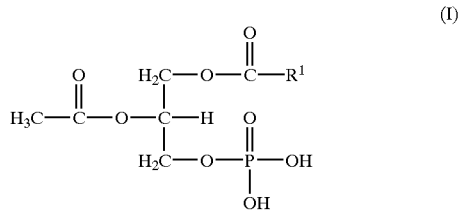

(I)

(wherein $R^1$ represents straight-chain alkyl having an odd number of carbon atoms, straight-chain alkenyl having an odd number of carbon atoms, or straight-chain alkynyl having an odd number of carbon atoms).

(15) A method for stimulating hair growth in a mammal, which comprises applying to the skin of said mammal the phosphatidic acid according to the above (14), and one or more members selected from the group consisting of proanthocyanidin, tocopherol, derivatives of tocopherol, pantothenic acid, derivatives of pantothenic acid, protein kinase C-specific inhibitors or pharmaceutically acceptable salts thereof and biotin.

DETAILED DESCRIPTION OF THE INVENTION

In the definition of each group in formula (I), the straight-chain alkyl having an odd number of carbon atoms includes those having 1 to 23, preferably 7 to 19 carbon atoms, such as methyl, propyl, pentyl, heptyl, nonyl, undecyl, tridecyl, pentadecyl, heptadecyl, nonadecyl, heneicosyl and tricosyl. Preferred are undecyl, tridecyl, pentadecyl and heptadecyl. The straight-chain alkenyl having an odd number of carbon atoms includes those having 3 to 23, preferably 7 to 19 carbon atoms, such as allyl, 1-propenyl, 2-pentenyl, 4-pentenyl, pentadienyl, heptenyl, nonenyl, undecenyl, tridecenyl, pentadecenyl, heptadecenyl, nonadecenyl, heneicosenyl and tricosenyl. Preferred are pentadecenyl and heptadecenyl. The straight-chain alkynyl having an odd number of carbon atoms includes those having 3 to 23, preferably 7 to 19 carbon atoms, such as propynyl, pentynyl, heptynyl, nonyl, undecynyl, tridecynyl, pentadecynyl, heptadecynyl, nonadecynyl, heneicosynyl and tricosynyl. The number and position of unsaturated bonds in the alkenyl and the alkynyl are not specifically restricted.

The phosphatidic acids to be used in the present invention can be obtained mainly by chemical synthesis [refer to Journal of Biological Chemistry, 189, 235–247 (1951)]. That is, the phosphatidic acids can be obtained by introducing a fatty acid to the 1-position of glycerin and then introducing an acetyl group to the 2-position of glycerin, followed by phosphorylation of glycerin at the 3-position. In each step of the synthesis, a protecting group may be introduced as may be required. The desired phosphatidic acids can also be obtained by enzymatic hydrolysis of phospholipid derivatives. For example, when a derivative of phosphatidyl choline is employed as a starting material, the desired phosphatidic acid can be obtained by hydrolyzing the phosphate bond with choline using an enzyme such as phospholipase D [Harumi Okuyama, Biochemistry of Lipids (Lectures on Biochemical Experiments 3), The Japanese Biochemical Society, p. 289, Tokyo Kagaku Dojin (1974)]. However, the methodology for the production of phosphatidic acids is not limited to the above-mentioned methods, and the above phosphatidic acids obtained by any methods may be used in the present invention.

The proanthocyanidin used in the present invention is a polymer composed of flavan-7-ol derivatives represented by formula (III):

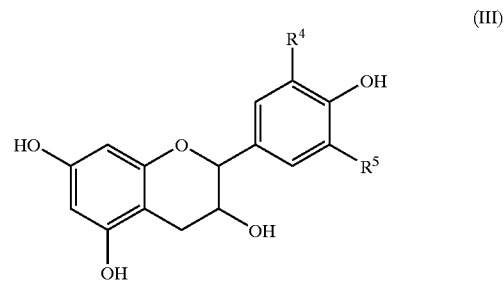

(III)

(wherein $R^4$ and $R^5$, which may be the same or different, each represents a hydrogen atom or a hydroxyl group) or the like as constitutive units.

Examples of the flavan-7-ol derivatives include catechin, epicatechin, gallocatechin, epigallocatechin, afzelechin, epi-afzelechin and any optical isomers thereof. Proanthocyanidin composed of epicatechin or catechin as a constitutive unit is preferably used in the present invention.

The bonding mode of the flavan-7-ol derivatives represented by formula (III) may be any mode. An example of a dimer composed of two flavan-7-ol derivatives is the one which has a bonding mode represented by formula (IV):

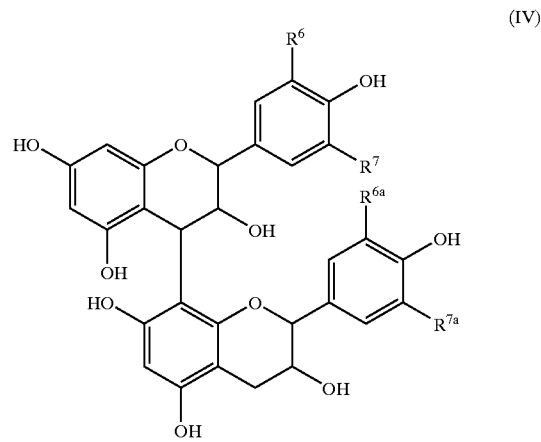

(IV)

(wherein $R^6$ and $R^{6a}$ have the same significance as the above $R^4$ and $R^7$ and $R^{7a}$ have the same significance as the above $R^5$). In trimers and higher polymers, the flavan-7-ol derivatives may be bonded in the same or different bonding modes.

The proanthocyanidin to be used in the present invention may be any dimer or higher polymer of flavan-7-ol derivatives, and is preferably a 2- to 10-mer, more preferably a 2- to 5-mer, further preferably a dimer or trimer. Examples of the dimers of flavan-7-ol derivatives include epicatechin-catechin co-dimers such as epicatechin-(4β→8)-catechin, epicatechin dimers such as epicatechin-(4β→8)-epicatechin, and catechin dimers such as catechin-(4α→8)-catechin. Examples of the trimers of flavan-7-ol derivatives include epicatechin trimers such as epicatechin-(4β→8)-epicatechin-(4β→8)-epicatechin, catechin trimers such as catechin-(4α→8)-catechin-(4α→8)-catechin, and epicatechin-catechin co-trimers such as epicatechin-(4β→8)-epicatechin-(4β→8)-catechin.

The proanthocyanidin to be used in the present invention also includes compounds wherein gallic acid or a sugar such as glucose or rhamnose is attached to the above proanthocyanidin.

Proanthocyanidin can be obtained by extraction and purification from various plants such as grape, apple, barley, Japanese persimmon, coconut, cacao, pine, azuki bean and peanut belonging to the genera Vitis, Malus, Hordeum, Diospyros, Cocos, Theobroma, Pinus, Phaseolus, Arachis and the like, or by chemical synthesis.

For instance, proanthocyanidin can be extracted and purified from plants according to the following known method.

Fruits, seeds, leaves, stalks, roots, rootstocks, etc. of the plants as starting materials are harvested at a suitable stage and used, as such or usually after being subjected to drying such as air drying, as materials for extraction. Extraction of proanthocyanidin from dry plants can be carried out in a manner similar to known methods [Chemical & Pharmaceutical Bulletin, 3, 3218 (1990); ibid., 40, 889–898 (1992)].

That is, the materials are ground or cut into fine pieces, followed by extraction with a solvent. Suitable solvents for extraction include hydrophilic or lipophilic solvents such as water, alcohols (e.g. ethanol, methanol and isopropyl alcohol), ketones (e.g. acetone and methyl ethyl ketone) and esters (e.g. methyl acetate and ethyl acetate), which can be used alone or as a mixture. The temperature for extraction is usually 0 to 100° C., preferably 5 to 500° C. The time for extraction is about one hour to 10 days, and the amount of the solvent is usually 1 to 30 times by weight, preferably 5 to 10 times by weight based on the dry material. Extraction is carried out by stirring or by dipping followed by standing, and is repeated twice or 3 times, as may be required.

The crude extract obtained in the above manner is filtered or centrifuged to remove the insoluble residue. Purification of proanthocyanidin from the thus treated extract, or from juice or sap of the plants can be carried out by any known purification methods. It is preferred to employ the two-phase solvent partitioning method, column chromatography, preparative high-performance liquid chromatography, etc. alone or in combination. The two-phase solvent partitioning methods include, for example, a method in which oil-soluble components and pigments are removed from the above extract by extraction with n-hexane, petroleum ether, etc., and a method in which proanthocyanidin is collected from the extract into the solvent phase by partition between a solvent such as n-butanol or methyl ethyl ketone and water. Column chromatography includes a method using normal phase silica gel, a method using reversed phase silica gel, adsorption column chromatography using as a carrier Diaion HP-20, Sepabeads SP-207 or the like, and gel filtration using as a carrier Sephadex LH-20 or the like. They are employed alone or in combination, if necessary repeatedly. Preparative high-performance liquid chromatography includes a method using a reversed phase column packed with octadecyl silica or the like, and a method using a normal phase column packed with silica gel or the like.

Proanthocyanidin can be purified by removing water-soluble ionic substances such as salts, nonionic substances such as saccharides and polysaccharides, oils, pigments, etc. from the above extract according to the above purification methods.

Grape-derived proanthocyanidin can be extracted and purified according to the method described in Acta Dermato Venereologica, 78, 428–432 (1998) or a similar method. Procyanidin B-1 [epicatechin-(4β→8)-catechin] procyanidin B-2 [epicatechin-(4β→8)-epicatechin], procyanidin B-3 [catechin-(4α→8)-catechin], procyanidin C-1 [epicatechin-(4β→8)-epicatechin-(4β→8)-epicatechin] and procyanidin C-2 [catechin-(4α→8)-catechin-(4α→8)-catechin] can be extracted and purified according to the method described in The Journal of Investigative Dermatology, 112, 310–316 (1999) or a similar method.

Production of proanthocyanidin by chemical synthesis can be carried out according to the method described in Journal of Chemical Society, Perkin Transaction I, 1535–1543 (1983) in which a process of producing dimers of epicatechin or catechin is described, the method described in Phytochemistry, 25, 1209–1215 (1986) or similar methods.

When proanthocyanidin is used as an active ingredient in the present invention, one or more kinds of proanthocyanidin may be used alone or as a mixture. It is preferred to use one or more members selected from the group consisting of grape-seed-derived proanthocyanidin, apple-derived proanthocyanidin, barley-derived proanthocyanidin, pine-derived proanthocyanidin, purified procyanidin oligomers, procyanidin B-1, procyanidin B-2, procyanidin B-3, procyanidin C-1 and procyanidin C-2. Specifically it is preferred to use one or more members selected from the group consisting of procyanidin B-1, procyanidin B-2, procyanidin B-3, procyanidin C-1 and procyanidin C-2.

The tocopherol and derivatives of tocopherol to be used in the present invention include any natural and synthetic ones that are commercially available, and derivatives such as acetic acid esters and nicotinic acid esters. Examples thereof include dl-α-tocopherol, d-α-tocopherol, dl-α-tocopherol acetate, d-α-tocopherol acetate and dl-α-tocopherol nicotinate.

The pantothenic acid and derivatives of pantothenic acid to be used in the present invention include any natural and synthetic ones that are commercially available and any other ones. Examples thereof include calcium pantothenate, sodium pantothenate, D-pantothenyl alcohol, DL-pantothenyl alcohol and pantothenyl ethyl ether.

As the protein kinase C-specific inhibitor in the present invention, any inhibitor that specifically inhibits protein kinase C can be used. It is preferred to use protein kinase inhibitors of which the ratio of the 50% protein kinase A (PKA) inhibition constant (hereinafter referred to as PKA-$IC_{50}$) to the 50% protein kinase C (PKC) inhibition constant (hereinafter referred to as PKC-$IC_{50}$) (the ratio is hereinafter referred to as PKA-$IC_{50}$PKC-$IC_{50}$) is 3 or more, preferably 3 to $10^9$, more preferably 10 to $10^9$, when PKC-inhibiting activity and PKA-inhibiting activity are measured by the following methods for measuring PKC-inhibiting activity and PKA-inhibiting activity. Examples thereof are one or more members selected from the group consisting of calphostin C, hexadecylphosphocholine, palmitoyl-DL-carnitine, polymyxin B and pharmaceutically acceptable salts thereof.

Examples of the pharmaceutically acceptable salts are hydrochlorides, hydrobromides, sulfates, nitrates, formates, acetates, benzoates, maleates, fumarates, succinates, tartrates, citrates, oxalates, methanesulfonates, toluenesulfonates, aspartates and glutamates.

The methods for measuring PKC-inhibiting activity and PKA-inhibiting activity are described below.

(1) Method for Measuring PKC-inhibiting Activity

Measurement of PKC-inhibiting activity can be carried out in a manner similar to the method of Kikkawa, et al. [Journal of Biological Chemistry, 257, 13341 (1982)].

To 250 µl of an aqueous solution comprising 2.5 µmol of magnesium acetate, 50 µg of histone Type IIIS (Sigma Chemical Co., Ltd.), 20 µg of phosphatidylserine, 0.8 µg of diolein, 25 nmol of calcium chloride, 5 µg of a crude enzyme (partially purified from rat brain by the method of Kikkawa, et al.) and 5 µmol of Tris-HCl buffer (pH 7.5) is added the above aqueous solution containing a test compound (10 µl), followed by incubation at 30° C. for 3 minutes. After the incubation, 1.25 nmol of [$\gamma$-$^{32}$P]ATP (5–10×10$^3$ cpm/nmol) is added thereto, followed by phosphorylation reaction at 30° C. for 3 minutes. The reaction is terminated by addition of 25% trichloroacetic acid and the reaction mixture is filtered through a cellulose acetate membrane (pore size: 0.45 µm, Toyo Filter Co., Ltd.) After the membrane is washed four times with 5% trichloroacetic acid, the radioactivity remaining on the membrane is measured as a test compound value. Separately, the above procedure is carried out in the same manner without addition of the test compound and the radioactivity is measured as a control value.

The molar concentration of the test compound giving a test compound value which is 50% of the control value is regarded as the 50% PKC inhibition constant (PKC-IC$_{50}$).

(2) Method for Measuring PKA-inhibiting Activity

Measurement of PKA-inhibiting activity can be carried out in a manner similar to the method of Kuo, et al. [Biochemistry, 64, 1349 (1969)].

To 250 µl of an aqueous solution comprising 5 µmol of Tris-HCl buffer (pH 6.8), 2.5 µmol of magnesium acetate, 100 µg of histone Type IIS (Sigma Chemical Co., Ltd.), 0.25 nmol of c-AMP and 200 µg of a crude enzyme (partially purified from calf heart by the method of Kuo, et al.) is added the above aqueous solution containing a test compound (10 µl), followed by incubation at 30° C. for 3 minutes. After the incubation, 1.25 nmol of [$\gamma$-$^{32}$P]ATP (5–10×10$^3$ cpm/nmol) is added thereto, followed by phosphorylation reaction at 30° C. for 3 minutes. The reaction is terminated by addition of 25% trichloroacetic acid and the reaction mixture is filtered through a cellulose acetate membrane (pore size: 0.45 µm, Toyo Filter Co., Ltd.) After the membrane is washed four times with 5% trichloroacetic acid, the radioactivity remaining on the membrane is measured as a test compound value. Separately, the above procedure is carried out in the same manner without addition of the test compound and the radioactivity is measured as a control value.

The molar concentration of the test compound giving a test compound value which is 50% of the control value is regarded as the 50% PKA inhibition constant (PKA-IC$_{50}$).

As the biotin, any natural or synthetic biotin that is commercially available can be used. Suitable examples thereof include D-biotin.

The hair-growing agent of the present invention may be in any preparation form so long as it can contain a phosphatidic acid, or phosphatidic acid and one or more members selected from the group consisting of proanthocyanidin, tocopherol, derivatives of tocopherol, pantothenic acid, derivatives of pantothenic acid, protein kinase C-specific inhibitors or pharmaceutically acceptable salts thereof, and biotin. For example, it can be used in the form of a liquid or solid hair-growing preparation containing a suitable pharmaceutical vehicle.

Examples of the liquid or solid hair-growing preparations include liquid preparations such as hair liquid, hair tonic and hair lotion, and solid preparations such as ointment and hair cream. These preparations can be produced by adding to a suitable vehicle a phosphatidic acid, or phosphatidic acid and one or more members selected from the group consisting of proanthocyanidin, tocopherol, derivatives of tocopherol, pantothenic acid, derivatives of pantothenic acid, protein kinase C-specific inhibitors or pharmaceutically acceptable salts thereof, and biotin, according to a conventional method.

The content of a phosphatidic acid in the hair-growing agent of the present invention widely varies depending upon the kind of the phosphatidic acid and the percutaneous absorbability derived from physical properties, but it is usually, alone or as a mixture, 0.01 to 5.0 wt % (hereinafter referred to merely as %), preferably 0.01 to 3.0%, more preferably 0.1 to 1.0%. The content of proanthocyanidin varies depending upon the purification degree, but is usually 0.01 to 10.0%, preferably 0.1 to 5.0%, more preferably 0.3 to 2.0%. The content of tocopherol or a derivative of tocopherol is usually 0.01 to 2%, preferably 0.05 to 2%, more preferably 0.05 to 1%. The content of pantothenic acid or a derivative of pantothenic acid is usually 0.01 to 2%, preferably 0.05 to 1%, more preferably 0.1 to 0.5%. The content of a protein kinase C-specific inhibitor or a pharmaceutically acceptable salt thereof widely varies depending upon the inhibitory activity and the percutaneous absorbability derived from physical properties, but it is usually, alone or as a mixture, 0.00001 to 1%, preferably 0.0001 to 1%, more preferably 0.001 to 0.1%. The content of biotin is usually 0.0001 to 0.1%, preferably 0.001 to 0.1%, more preferably 0.001 to 0.05%.

Preferred vehicles for liquid preparations are those which are generally used in hair-growing agents such as purified water, ethyl alcohol and polyvalent alcohols. If necessary, additives may be added thereto.

Examples of the polyvalent alcohols are glycerol, 1,3-butylene glycol and propylene glycol.

Additives include surfactants, vitamins, anti-inflammatory agents, microbicides, hormones, crude drug extracts, tinctures, refrigerants, moisturizers, antioxidants, sequestering agents and perfumes.

Examples of the surfactants are polyoxyethylene (60) hardened castor oil, polyoxyethylene (8) oleyl ether, polyoxyethylene (10) oleyl ether, polyoxyethylene (10) monooleate, polyoxyethylene (30) glyceryl monostearate, sorbitan monostearate, polyoxyethylene (20) sorbitan monooleate, sucrose fatty acid esters, hexaglycerin monooleate, hexaglycerin monolaurate, polyoxyethylene reduced lanolin, polyoxyethylene (20) lanolin alcohol, polyoxyethylene (25) glyceryl pyroglutamate isostearate, and N-acetylglutamine isostearyl ester.

Examples of the vitamins are benzyl nicotinate, nicotinamide, pyridoxine hydrochloride and riboflavin.

Examples of the anti-inflammatory agents are dipotassium glycyrrhizinate, β-glycyrrhetinic acid, allantoin, diphenhydramine hydrochloride, guaiazulene and 1-menthol.

Examples of the microbicides are trichlorohydroxydiphenyl ether, hinokitiol, triclosan, chlorohexidine gluconate, phenoxyethanol, resorcin, isopropylmethylphenol, azulene, salicylic acid, zinc pyrithione, benzalkonium chloride, photosensitizing dye No. 301 and sodium mononitroguaiacol.

Examples of the hormones are ethynylestradiol, estrone and estradiol.

Examples of the crude drug extracts are extract of *Swertia japonica* Makino, garlic extract, ginseng extract, aloe extract, cinchona extract, plant worm extract and saffron extract.

Examples of the tinctures are capsicum tincture, ginger tincture and cantharis tincture.

Examples of the refrigerants are capsicum tincture, 1-menthol and camphor.

Examples of the moisturizers are L-pyrrolidonecarboxylic acid, sodium hyaluronate and chondroitin sulfate.

Examples of the antioxidants are butylhydroxyanisole, isopropyl gallate, propyl gallate and erythorbic acid.

Examples of the sequestering agents are ethylenediamine tetraacetate and salts thereof.

Examples of the perfumes are natural perfumes such as orange oil, lemon oil, bergamot oil, lime oil, lemongrass oil and lavender oil, and synthetic perfumes such as menthol, rose oxide, linalool, citral and linalyl acetate.

When the above liquid preparations are used as spray, they can be used in combination with combustible gas, incombustible gas, or the like. Examples of the combustible gas are LPG (a liquefied petroleum gas) and dimethyl ether, and examples of the incombustible gas are a nitrogen gas and a carbon dioxide gas.

Vehicles for solid preparations include Vaseline, solid paraffin, vegetable oils, mineral oils, lanolin, wax and macrogol. Further, the above additives, and lower alcohols such as ethyl alcohol and isopropyl alcohol may be added thereto, if necessary.

The dose of the hair-growing agent of the present invention varies depending upon the age or the body weight of a patient, the symptom of the disease, the therapeutic effect, the mode of administration, the time of treatment or the like. The agent is percutaneously administered in an amount of 0.1 to 250 mg, preferably 1 to 100 mg in terms of phosphatidic acid per adult once to several times per day.

Certain embodiments of the present invention are illustrated in the following examples.

BEST MODES FOR CARRYING OUT THE INVENTION

EXAMPLE 1

Preparation of Compositions 1 and 2

| | |
|---|---|
| 1-O-Oleoyl-2-O-acetylglyceryl-3-phosphoric acid | 0.4% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

To the above mixture was added purified water to make up to 100%. The mixture was made homogeneous with stirring to prepare composition 1.

Composition 2 was prepared in the same manner as above except that purified water was used instead of 1-O-oleoyl-2-O-acetylglyceryl-3-phosphoric acid.

EXAMPLE 2

Preparation of Compositions 3 and 4

| | |
|---|---|
| 1-O-Oleoyl-2-O-acetylglyceryl-3-phosphoric acid | 0.4% |
| Procyanidin B-2 | 1% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

Procyanidin B-2 was produced according to the method described in The Journal of Investigative Dermatology, 112, 310–316 (1999).

To the above mixture was added purified water to make up to 100%. The mixture was made homogeneous with stirring to prepare composition 3.

Composition 4 was prepared in the same manner as above except that purified water was used instead of 1-O-oleoyl-2-O-acetylglyceryl-3-phosphoric acid.

EXAMPLE 3

Preparation of Compositions 5 and 6

| | |
|---|---|
| 1-O-Oleoyl-2-O-acetylglyceryl-3-phosphoric acid | 0.4% |
| dl-α-Tocopherol | 1.0% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

To the above mixture was added purified water to make up to 100%. The mixture was made homogeneous with stirring to prepare composition 5.

Composition 6 was prepared in the same manner as above except that purified water was used instead of 1-O-oleoyl-2-O-acetylglyceryl-3-phosphoric acid.

EXAMPLE 4

Preparation of Compositions 7 and 8

| | |
|---|---|
| 1-O-Oleoyl-2-O-acetylglyceryl-3-phosphoric acid | 0.4% |
| Pantothenyl ethyl ether | 0.3% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

To the above mixture was added purified water to make up to 100%. The mixture was made homogeneous with stirring to prepare composition 7.

Composition 8 was prepared in the same manner as above except that purified water was used instead of 1-O-oleoyl-2-O-acetylglyceryl-3-phosphoric acid.

EXAMPLE 5

Preparation of Compositions 9 and 10

| | |
|---|---|
| 1-O-Oleoyl-2-O-acetylglyceryl-3-phosphoric acid | 0.4% |
| Biotin | 0.05% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

To the above mixture was added purified water to make up to 100%. The mixture was made homogeneous with stirring to prepare composition 9.

Composition 10 was prepared in the same manner as above except that purified water was used instead of 1-O-oleoyl-2-O-acetylglyceryl-3-phosphoric acid.

Reference Example 1

Synthesis of 1-O-oleoyl-2-O-acetylglyceryl-3-phosphoric Acid (1-O-oleoyl-2-O-acetylphosphatidic Acid)

Synthesis of 1-O-oleoyl-2-O-acetylglyceryl-3-phosphoric acid can be carried out according to the method described in Journal of Medicinal Chemistry, 2038–2044 (1986) or a similar method.

To a mixture of phosphorus oxychloride (700 µl), triethylamine (1000 µl) and hexane (50 ml) was added dropwise a solution of 1-O-oleoyl-2-O-acetylglycerol (20.0 mg, Funakoshi Co., Ltd.) in chloroform (8.0 ml) with stirring at room temperature. After 15 hours of stirring, 10 ml of purified water was added thereto, followed by further stirring at room temperature for one hour. The organic layer was separated and developed on a silica gel thin layer chromatography plate with a mobile phase of chloroform:methanol:acetic acid:water=170:25:25:6. A band of silica gel containing the desired product was scraped off and diethyl ether was added to this silica gel powder. The organic layer was separated and concentrated under reduced pressure to obtain 55 mg of 1-O-oleoyl-2-O-acetylglyceryl-3-phosphoric acid.

The activity of the hair-growing agent of the present invention is shown in detail by the following test examples.

Test Example 1

Cell Growth-Promoting Effect on Cultured Mouse Hair Follicle Epithelial Cells

Mouse hair follicle epithelial cells were separated and cultured according to a modification of the method of Tanigaki, et al. [Archives of Dermatological Research, 284, 290–296 (1992)].

The skin on the back of a 4-days-old C3H mouse (Charles River Japan, Inc.) was cut off and treated with MEM (Eagle's Minimum Essential Medium) containing 500 units/ml Dispase (Godo Shusei Co., Ltd.) and 5% fetal calf serum (FCS) at 4° C. for 16 hours.

Then, the epidermis was stripped from the skin section, and the obtained dermis layer was treated with DMEM (Dulbecco's modified Eagle Medium) containing 0.25% Collagenase N-2 (Nitta Gelatin Co., Ltd.) and 10% FCS at 37° C. for one hour to obtain a dermis suspension. The dermis suspension was filtered through a 212-µm nylon mesh (Nippon Rikagaku Kikai Co., Ltd.) and the filtrate was centrifuged at 1000 rpm for 5 minutes to obtain pellets containing hair follicle tissue. To the pellets was added calcium/magnesium-free PBS (Dulbecco's Phosphate-Buffered Saline) and the pellets were suspended therein using a pipette. The resulting suspension was allowed to stand for 15 minutes to precipitate hair follicle tissue. The same procedure as above (addition of calcium/magnesium-free PBS, suspending by use of a pipette, and precipitation by allowing the suspension to stand for 15 minutes) was repeated three times using the obtained hair follicle tissue.

Then, the hair follicle tissue was treated with a solution containing 0.1% ethylenediaminetetraacetic acid (EDTA) and 0.25% trypsin (Gibco) at 37° C. for 5 minutes. To the resulting mixture was added DMEM containing 10% FCS to prepare a hair follicle tissue cell suspension having a density of $3 \times 10^5$ cells/ml. The hair follicle tissue cell suspension was put into wells of a 24-well collagen-coated plate (Iwaki Glass Co., Ltd.) in an amount of 1 ml/well, followed by culturing in 5% $CO_2$ at 37° C. for 24 hours.

After culturing, the medium was replaced by a medium prepared by adding to MCDB153 medium (Kyokuto Pharmaceutical Ind. Co., Ltd.) DMSO containing 5 mg/l bovine insulin (Sigma Chemical Co., Ltd.); 5 µg/l mouse epidermal growth factor (EGF) (Takara Shuzo Co., Ltd.); 40 mg/l bovine pituitary extract (Kyokuto Pharmaceutical Ind. Co., Ltd.); 10 mg/l human transferrin (Sigma Chemical Co., Ltd.); 0.4 mg/l hydrocortisone (Sigma Chemical Co., Ltd.); 0.63 µg/l progesterone (Collaborative Research Co.); 14 mg/l O-phosphoethanolamine (Sigma Chemical Co., Ltd.); 6.1 mg/l ethanolamine (Sigma Chemical Co., Ltd.); 50 U/ml penicillin (Wako Pure Chemical Industries, Ltd.); 50 µg/ml streptomycin (Wako Pure Chemical Industries, Ltd.); 1-O-oleoyl-2-O-acetylglyceryl-3-phosphoric acid obtained in Reference Example 1, and/or procyanidin B-2 or dl-α-tocopherol (added in an amount of 1/100 by volume), followed by further culturing in 5% $CO_2$ at 37° C. for 5 days. During the culturing, the medium was replaced with a fresh one every other day.

As a control, the cells were cultured in the same medium as above except that DMSO alone was added in an amount of 1/100 by volume in place of DMSO containing 1-O-oleoyl-2-O-acetylglyceryl-3-phosphoric acid, and/or procyanidin B-2 or dl-α-tocopherol.

The degree of cell growth was measured according to the method using MTT [3-(4,5-dimethylthiazol-2-yl)-2,5-diphenyl tetrazolium bromide] [Experimental Medicine (extra number), Bio Manual UP Series, Experimental Method of Cell Culture for Molecular Biological Studies, p. 89–92, Yodosha (1995)].

To each well of the 24-well microplate (2 cm$^2$/well) was added a PBS solution of MTT (5 mg/ml) in an amount of 1/10 by volume based on 1 ml of the culture. The plate was shaken to make the mixture homogeneous, followed by culturing in 5% $CO_2$ at 37° C. for 4 hours. Four hours later, the culture was sucked and 1 ml of a 0.04 mol/l solution of HCl in isopropyl alcohol was added to each well to completely dissolve formazan formed in the wells.

The degree of cell growth was determined by measuring the absorbance at 570 nm based on that at 650 nm as a control.

The cell growth-promoting activity of the compounds used in the present invention is shown in Table 1.

TABLE 1

| Test group | Active ingredient (concentration) | Relative cell growth rate based on the control as 100 |
| --- | --- | --- |
| 1 | 1-O-Oleoyl-2-O-acetylglyceryl-3-phosphoric acid (1 µmol/l) | 327 |
| 2 | Procyanidin B-2 (30 µmol/l) | 295 |
| 3 | dl-α-Tocopherol (30 µmol/l) | 178 |
| 4 | Compound of test group 1 (1 µmol/l) + procyanidin B-2 (30 µmol/l) | 368 |
| 5 | Compound of test group 1 (1 µmol/l) + dl-α-tocopherol (30 µmol/l) | 351 |

As shown in Table 1, the phosphatidic acid used in the present invention exhibited a significant growth-promoting activity on mouse hair follicle epithelial cells. The growth-promoting activity of proanthocyanidin and tocopherol on mouse hair follicle epithelial cells was reinforced by using them together with the above phosphatidic acid.

Test Example 2

Effect on Hair Growth of Mouse

A test of the effect on hair growth of mice was carried out referring to the method of ogawa, et al. [The Journal of Dermatology, 10, 45–54, (1983)].

Nine-weeks-old male C3H/HeSlc mice whose hair cycle was in the telogen were divided into groups each consisting of 4 or 5 mice. Hair on the back of each mouse was shaven using electric hair clippers and an electric shaver. Then, compositions 1 to 10 prepared in Examples 1 to 5 were applied on the shaven part in an amount of 200 μl once per day. To the mice of control group was applied composition 2 in the same manner.

On the 18th day after the start of the test, the on the back of each mouse was cut off and graphed. Using an image processor (Avionics Co., Spicca II), percentage of the hair-grown area to the tot area of the skin on the back was calculated. The rate of the increased hair-grown area (%) was obtained by subtracting the hair-growing rate of the control group from the hair-growing rate of the test group.

The results are shown in Table 2.

TABLE 2

| Composition | Rate of incresed hair-grown area (%) |
|---|---|
| 2 (Control group) | 0 |
| 1 | 52 |
| 3 | 65 |
| 4 | 45 |
| 5 | 66 |
| 6 | 40 |
| 7 | 58 |
| 8 | 16 |
| 9 | 59 |
| 10 | 11 |

As shown in Table 2, the hair-growing agents compromising phosphatidic acid of the present invention exhibited a significant promoting effect on the hair growth of mouse. The promoting effect of proanthocyanidin, tocopherol, a derivative of pantothenic acid, and biotin on the hair growth of mouse was reinforced by using them together with a phosphatidic acid.

What is claimed is:

1. A hair-growing agent comprising, as an active ingredient, a phosphatidic acid represented by formula (I):

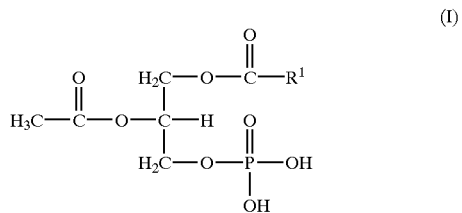

(I)

(wherein $R^1$ represents straight-chain alkyl having an odd number of carbon atoms, straight-chain alkenyl having an odd number of carbon atoms, or straight-chain alkynyl having an odd number of carbon atoms).

2. The hair-growing agent according to claim 1, wherein the straight-chain alkyl having an odd number of carbon atoms is undecyl, tridecyl, pentadecyl or heptadecyl, and the straight-chain alkenyl having an odd number of carbon atoms is pentadecenyl or heptadecenyl.

3. A hair-growing agent comprising, as active ingredients, the phosphatidic acid according to claim 1 or 2, and one or more members selected from the group consisting of proanthocyanidin, tocopherol, derivatives of tocopherol, pantothenic acid, derivatives of pantothenic acid, protein kinase C-specific inhibitors or pharmaceutically acceptable salts thereof and biotin.

4. The hair-growing agent according to claim 1 or 2, further comprising proanthocyanidin.

5. The hair-growing agent according to claim 4, wherein the proanthocyanidin is one or more members selected from the group consisting of procyanidin B-1, procyanidin B-2, procyanidin B-3, procyanidin C-1 and procyanidin C-2.

6. The hair-growing agent according to claim 4, further comprising tocopherol or a derivative of tocopherol.

7. The hair-growing agent according to claim 6, wherein the tocopherol or the derivative of tocopherol is one or more members selected from the group consisting of dl-α-tocopherol, d-α-tocopherol, dl-α-tocopherol acetate, d-α-tocopherol acetate and dl-α-tocopherol nicotinate.

8. The hair-growing agent according to claim 7, further comprising pantothenic acid or a derivative of pantothenic acid.

9. The hair-growing agent according to claim 8, wherein the pantothenic acid or the derivative of pantothenic acid is one or more members selected from the group consisting of calcium pantothenate, sodium pantothenate, D-pantothenyl alcohol, DL-pantothenyl alcohol and pantothenyl ethyl ether.

10. The hair-growing agent according to claim 9, further comprising a protein kinase C-specific inhibitor or a pharmaceutically acceptable salt thereof.

11. The hair-growing agent according to claim 10, wherein the protein kinase C-specific inhibitor is one or more members selected from the group consisting of calphostin C, hexadecylphosphocholine, palmitoyl-DL-carnitine and polymyxin B.

12. The hair-growing agent according to claim 11, further comprising biotin.

13. The hair-growing agent according to claim 12, which does not substantially comprise minoxidil.

14. A method for stimulating hair growth in a mammal, which comprises applying to the skin of said mammal a phosphatidic acid represented by formula (I):

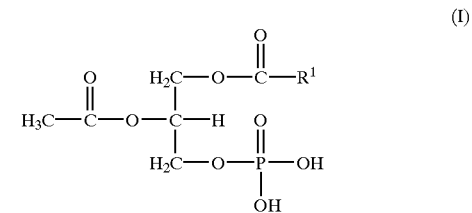

(I)

(wherein $R^1$ represents straight-chain alkyl having an odd number of carbon atoms, straight-chain alkenyl having an odd number of carbon atoms, or straight-chain alkynyl having an odd number of carbon atoms).

15. A method for stimulating hair growth in a mammal, which comprises applying to the skin of said mammal the phosphatidic acid according to claim 14, and one or more members selected from the group consisting of proanthocyanidin, tocopherol, derivatives of tocopherol, pantothenic acid, derivatives of pantothenic acid, protein kinase C-specific inhibitors or pharmaceutically acceptable salts thereof and biotin.

* * * * *